United States Patent
Maurer et al.

[11] Patent Number: 6,153,070
[45] Date of Patent: Nov. 28, 2000

[54] SENSOR PACKAGING USING HEAT STAKING TECHNIQUE

[75] Inventors: D. Joseph Maurer, Pearl City, Ill.; Said Karbassi, Monroe, Wis.; Richard W. Gehman, Freeport, Ill.

[73] Assignee: Honeywell Inc, Morristown, N.J.

[21] Appl. No.: 09/074,281

[22] Filed: May 7, 1998

[51] Int. Cl.[7] .................................................. G01N 27/26
[52] U.S. Cl. ............................................ 204/416; 206/706
[58] Field of Search .................................. 206/722, 706; 204/416, 418, 419, 400

[56] References Cited

U.S. PATENT DOCUMENTS

| | | |
|---|---|---|
| 4,449,011 | 5/1984 | Kratochvil et al. . |
| 4,851,104 | 7/1989 | Connery et al. ............... 204/406 |
| 5,068,205 | 11/1991 | Baxter et al. . |
| 5,184,107 | 2/1993 | Maurer . |

FOREIGN PATENT DOCUMENTS

| | | |
|---|---|---|
| 0 116 117 | 8/1984 | European Pat. Off. . |
| 0 307 973 | 3/1989 | European Pat. Off. . |
| 0 467 479 | 1/1992 | European Pat. Off. . |
| 297 04 357 U | 9/1997 | Germany . |

OTHER PUBLICATIONS

PCT, International Search Report, European Patent Office, Sep. 08, 1999, PCT/US99/09500.

*Primary Examiner*—T. Tung
*Assistant Examiner*—Alex Noguerola
*Attorney, Agent, or Firm*—Roland W. Norris; Andrew A. Abeyta

[57] ABSTRACT

An environmental sensor apparatus and method of making same is disclosed in which an environmentally sensitive silicon die is sandwiched between an elastomeric media seal and a conductive elastomeric pad contained within a housing. The conductive elastomeric pad contacts a printed circuit board (PCB) which leads from the housing. The die, elastomers and PCB are secured by a press fit plug which contacts the PCB and is heat staked to the housing to provide a substantially flush hermetic seal.

19 Claims, 6 Drawing Sheets

SENSOR PACKAGING USING HEAT STAKING TECHNIQUE

This application is related to commonly-owned, co-pending application Ser. No. 09/074,304, *Sensor Packaging Having an Integral Electrode Plug Member*, filed on May 6, 1998.

BACKGROUND OF THE INVENTION

1. Field of the Invention

The invention relates generally to method and apparatus for packaging sensors. The invention relates more particularly to environmental sensors, such as pH sensors, where a microelectronic substrate such as an ion sensitive field effect transistor (ISFET) must be exposed to often caustic or acidic media.

2. Discussion of the Related Art

Various ion sensitive field effect transistors (ISFET's), or microelectronic ion sensors, are known in the art. Such ISFET's have advantages for use as pH sensors such as being solid state, small size and relatively inexpensive to produce.

However, certain problems arise in utilizing the ISFET as a practical solution for low cost sensing applications. Among these are the encapsulation of the device in a body or housing suitable for utilizing the ISFET as part of an ion sensitive probe for commercial purposes. Typically, the ISFET is potted in epoxy so that the sensor electronics are not subjected to the often severe environment of the liquid being tested. Epoxy can be hard to work with in cases where the sensor is not completely potted because the sensor must incorporate a window where the electroactive element is exposed to the liquid. Further problems arise in bonding the microelectronic ISFET structure to a suitable substrate for connection to additional probe electronics.

Also, epoxies are often not available with a wide range of choices against corrosion by various media and hence are not applicable over a wide range of environments to which probes must be impervious. More over, highly caustic solutions can etch the die itself, rendering it suitable for only a single use. Probe cost then becomes of paramount importance in single use applications.

A known packaging technique for a pH sensor 11 may be seen by referring to FIGS. 1A and 1B, which may also be seen in U.S. Pat. Nos. 5,068,205 and 4,851,104, respectively. In this technique a glass header 12 has been utilized wherein the silicon die (ISFET) 17 is adhered to a first side 14 of a borosilicate glass carrier 16 over a through-hole 15 therein. The carrier 16 has a through-hole 15 in it to maintain uncovered the contact areas of the ISFET 17. The carrier 16 also has leads, collectively 18, on the second side 20 thereof to provide electrical access to the ISFET area from the edges of the carrier. The ISFET substrate 17 is electrostatically bonded to the glass carrier 14. Lead wires, collectively 22, are then bonded between the ISFET and the glass carrier leads. The glass carrier leads 18 and back of the ISFET 17 are then covered with a second glass plate 24 for protection. This header assembly 12 is then connected to a flexible circuit 26 for leading out through the probe body 28. This header 12 and circuit 26 assembly are then enclosed within the probe body 28 along with a counterelectrode 27, as detailed in U.S. Pat. No. 4,851,104, and potted with epoxy to isolate the internal components from the typically corrosive liquids of the sensing environment. Yield is low and assembly costs are high due to the brittle nature of the glass substrate, the time consuming nature of epoxy potting and assembly of the many pieces.

Hence there is need for an ion sensitive microelectronic sensor package which is easily and inexpensively contained in an impervious housing while permitting media access to the die by hermetically sealing the probe electronics from the harsh media environment. More generally there is a need for packaging techniques for sensing apparatus which eliminates the drawbacks of epoxy potting.

Certain techniques for encapsulating piezoresistive pressure transducers with a conductive elastomeric seal, are detailed in U.S. Pat. No. 5,184,107 to Maurer. This patent details a low cost piezoresistive pressure transducer utilizing premolded elastomeric seals in which at least one seal is electrically conductive. A piezoresistive stress sensitive element in the form of a diaphragm of semiconductor material having a thickened rim is held at its rim between a pair of premolded elastomeric seals in a two piece housing. Electrical connections with external circuitry are made by conductive paths through one of the elastomeric seals which makes contact with electrical leads which pass through the housing wall.

SUMMARY OF THE INVENTION

A low cost environmental sensor apparatus and method of making same are taught which are easily and inexpensively manufactured. An ion sensitive microelectronic substrate, or die, is manufactured which has an ion sensitive first surface and patterned electrical leads on its second service. The die is placed between two elastomeric seals, a first media seal, and a second conductive seal. This "sandwich" is then loaded, or placed under pressure, within a media impervious housing having a media through-hole therein. A PCB containing patterned electrical leads communicates electrically with the die through the selectively conductive second elastomeric seal. The first media seal through-hole communicates with the housing media through-hole thereby exposing the ion sensitive surface of the ISFET while protecting the other components of the sensor. A plug is then used to mechanically load the PCB, the elastomeric seals and the ISFET in position within the probe housing. The plug is then heat staked to the housing wall in such a fashion as to form a substantially flush outer wall of the housing with a hermetic seal. The heat staking technique of the present invention may be utilized in a variety of packaging applications where a hermetic seal is desired and largely eliminate the need for epoxy potting.

By simplifying the construction of the ion sensitive pH sensor great advantages are attained in yield and reliability while lowering the overall cost of the probe substantially.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Figure 1A:
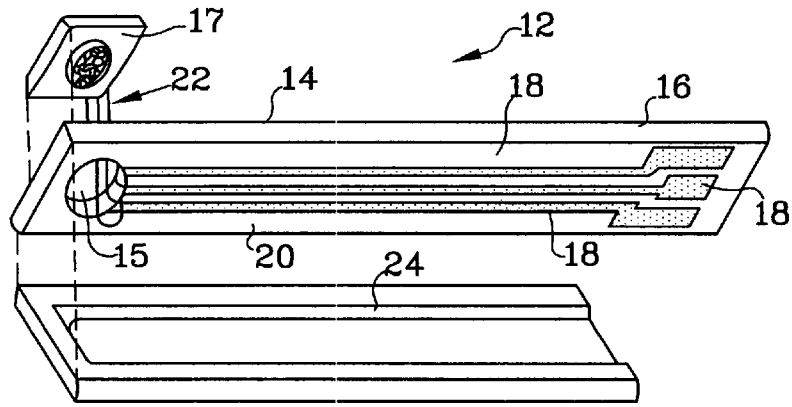
FIGS. 1A and 1B are representations of a known ISFET sensor.

Throughout the Description of the Preferred Embodiment, like components will be identified by like reference numerals.

Figure 2:
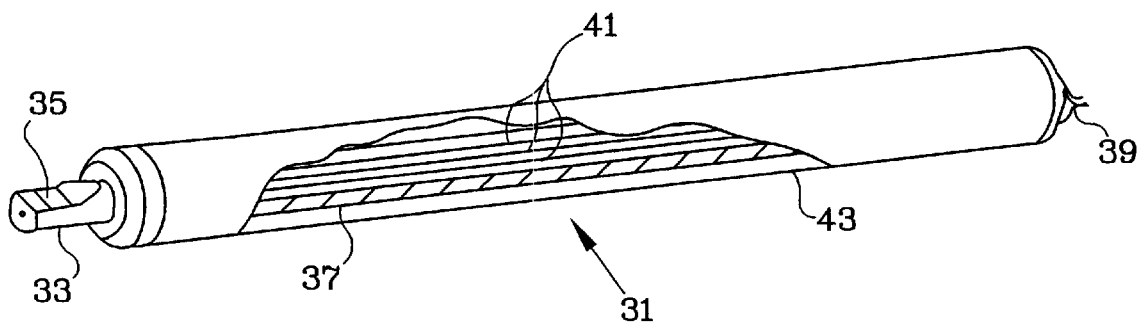
FIG. 2 is a partial cut-away perspective view of an embodiment of the end item probe according to the present invention.

Referring to FIG. 2 a sensor apparatus, taught herein the context of a pH sensor probe 31, has a ISFET housing 33 containing a media through-hole 35 therein. The housing 33 is composed of any thermoplastic engineering grade plastic suitable for the intended sensing environment. Extending from the ISFET housing 33 is a printed circuit board 37 ending at its distal end in electrical contact pins 39. The printed circuit board 37 makes electrical connection between electrical contact pins 39 and the ISFET (not shown) through printed wiring runs 41. Sealing the ISFET housing 33 and PCB 37 through the length of the probe 31 is a probe casing 43 made of a material selected to withstand the type of media environment to which the probe is to be exposed. The probe casing 43 is hermetically sealed to the ISFET housing as further explained below.

Figure 3:
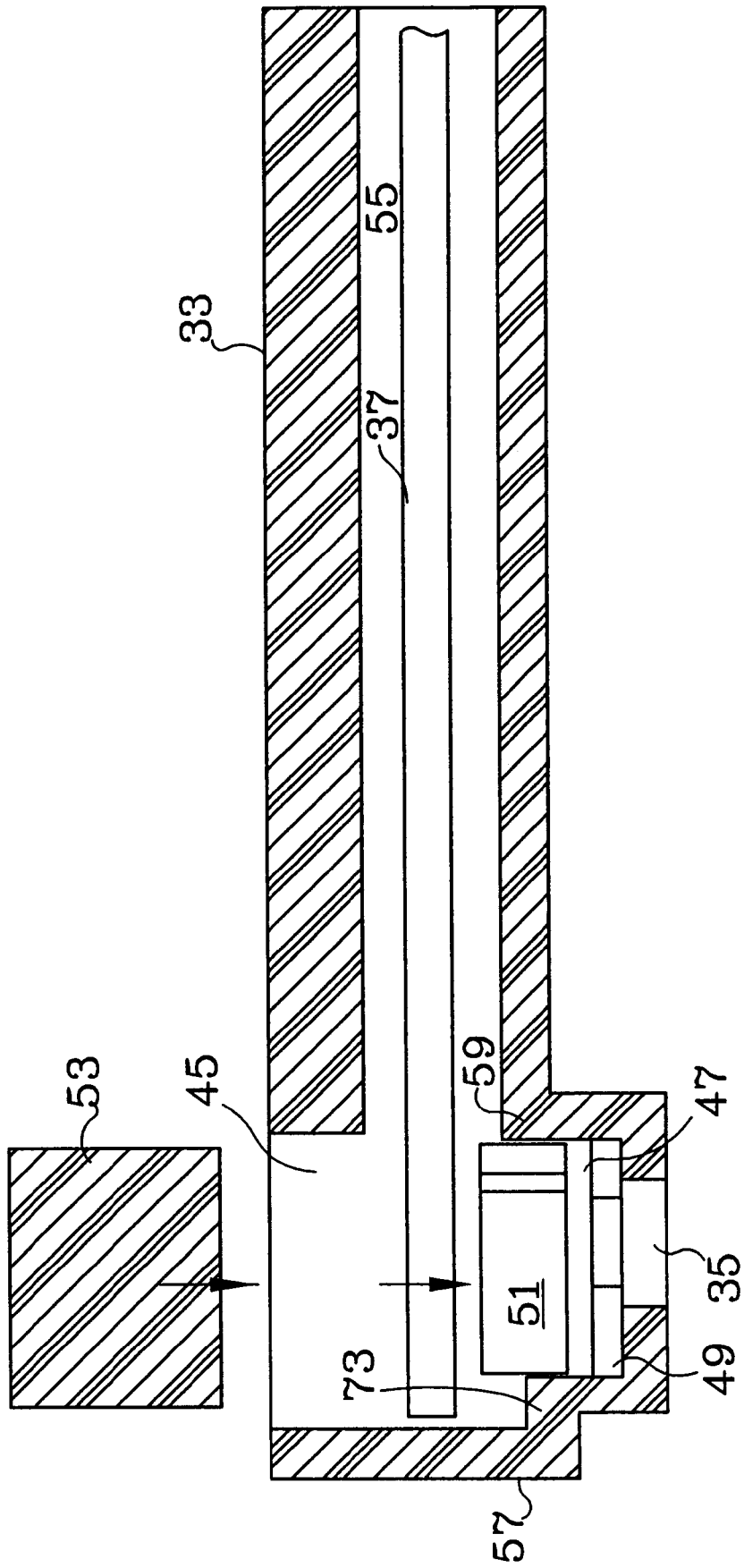
FIG. 3 is a cross sectional view of a partially completed probe according to the present invention.

As seen in the schematic cross section view of FIG. 3 the microelectronic ISFET housing 33 is a substantially cylindrically shaped housing with the media through-hole 35 on a first side thereof and an opposing through-hole 45 of substantially larger size to permit placement of the microelectronic die of the ISFET 47, the media seal 49 and conductive seal 51 as further explained below. The PCB 37 is further contained within the ISFET housing 33 as is the back plug 53. The back plug 53 and PCB 37 are both shown in intermediate in-work positions prior to completion of the assembled and sealed ISFET housing.

The central bore 55 of the ISFET housing 33 is enlarged at the proximal end 57 to provide a nesting well area 59 for containment of the ISFET 47 and elastomeric seals 49 and 51. The well 59 communicates with the media hole 35. The back hole 45 opposite the media hole 35 also communicates with the central bore 55, allowing the back plug 53 to contact the PCB 37 forcing it into contact with the conductive seal 51 when the back plug 53 is press fit in locking engagement with ISFET housing 33.

Figure 4:
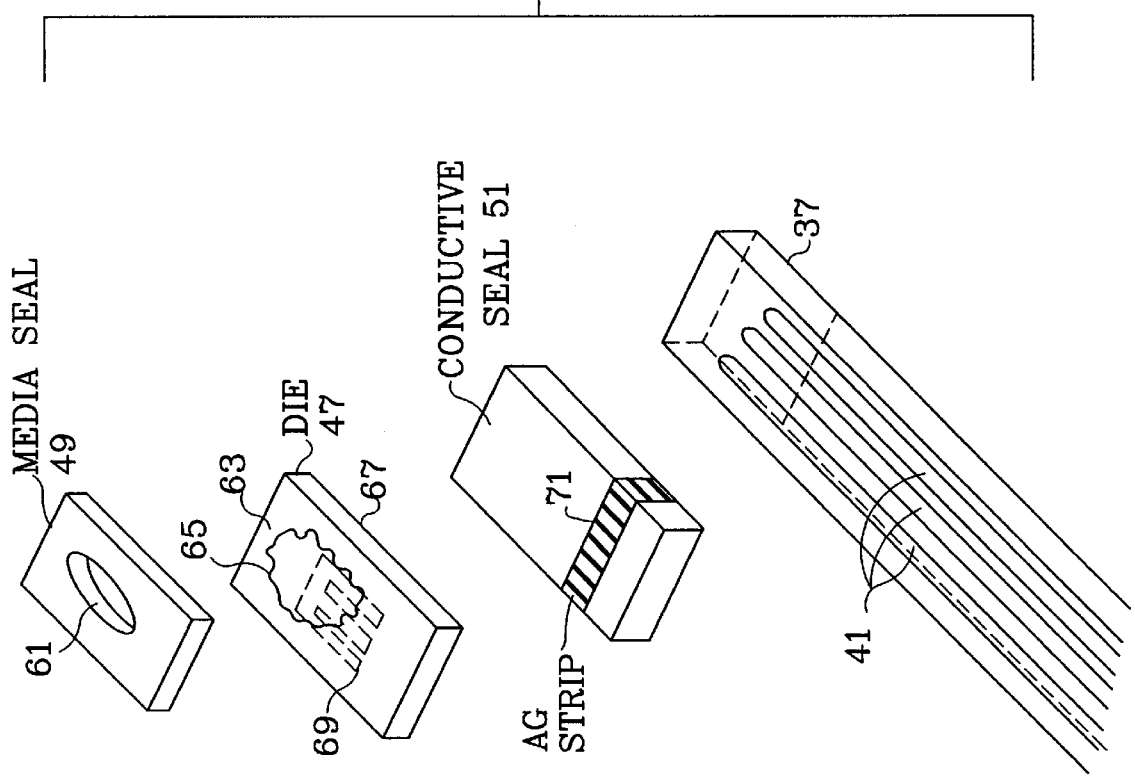
FIG. 4 is an exploded view of the media seal, microelectronic structure, conductive seal, and PCB of the present invention.

Referencing FIG. 4, the principle internal components of the pH probe: media seal 49, ISFET die 47, conductive seal 51 and PCB 37 with its printed wiring runs 49 are shown, from top to bottom, in the order of their placement inside ISFET housing 33 (not shown). The media seal 49 is sized to have its side walls fit in abutting contact with the walls of the nesting well 59. The media seal 49 has a central through-hole 61 for alignment with the media hole 35. The media seal is composed of an elastomeric material, impervious to the media which the sensor is designed to be emersed in. For example, ethylene propylene diene monomer (EDPM) of 50–60 durometer under 25% compression is used in the presently contemplated best mode.

The ISFET die 47 is designed to abut the media seal 49 on a first side 63 thereof which contains the ISFET sensing area 65 conditioned to be ion sensitive to the media to be sensed. A second side 67 of the die contains a patterned electrical leads 69 as necessary for the operation of the ISFET. Abutting the second side 67 of the die 47 is an elastomeric conductive seal 51 commercially known as a "silver stacks connector" with conductive silver strips 71 placed therein to allow electrical conduction in the Z axis, i.e. through the thickness of the conductive seal, thereby providing electrical connection between the die 47 and the printed wiring runs 41 of the PCB 37 when the components are loaded in opposition to each other within the ISFET housing (not shown).

Referring again to FIGS. 3 and 4, it can be seen that the media seal 49 is placed in the nesting well 59 which communicates with the media hole 35, with a major plane face of the seal substantially parallel to the long axis of the central bore 55. The ISFET 47 is then placed in the nesting well in contact with media seal 49 so that its ion sensing area 65 is aligned with the media seal through-hole 61, placing the patterned electrical lead 69 of the second ISFET surface 67 towards the central bore 55. Elastomeric conductive seal 51 is then placed in the nesting well 59 so that its silver conductive strips 71 contact the patterned electrical leads 69 of the ISFET 47. The elastomeric conductive seal 51 in its unloaded state rests slightly above the collar 73 of well 59 in its unloaded state. The PCB 37 is then inserted through the central bore of the ISFET housing 33 above the conductive seal 51. The PCB 37 is then tipped down to preload the seals 51 and 49 and the die 47 therebetween to the predetermined depth and/or compression of the collar 73. In the case of the pH probe a compression on the media seal of 25% has been found sufficient to prevent leaks. While the PCB is in this position, the back plug 53 is inserted through back hole 45 and mechanically locked in a press fit manner to the ISFET housing 33 while pressing the PCB 37 in loading contact with the conductive seal 51. The back plug 53 is then heat staked, as further explained below, to the ISFET body 33 providing a substantially flush outer wall and hermetic seal for the ISFET body 33 in the area of back hole 45. Flush mounting of the plug is preferred where the probe is to be immersed in a flowing liquid, but is not considered a necessity for mating the plug and housing outside surface in all embodiments of the present invention. All electrical components are locked in place with the elastomeric seals providing the necessary cushioning for the ISFET to prevent breakage thereof during mechanical operations.

Figure 5:
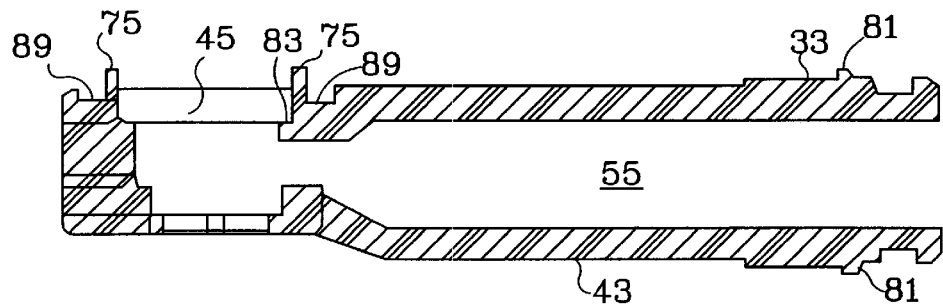
FIG. 5 is a cross section of the microelectronic structure pH sensor housing, in work before being sealed by a hermetically sealed heat stacked plug.
Figure 6:
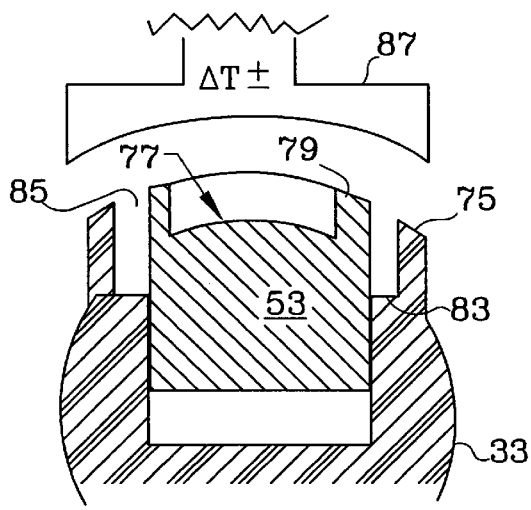
FIGS. 6 and 7 are a cross sectional view and a top perspective view of the sealing plug and housing of the present invention, respectively.
Figure 7:
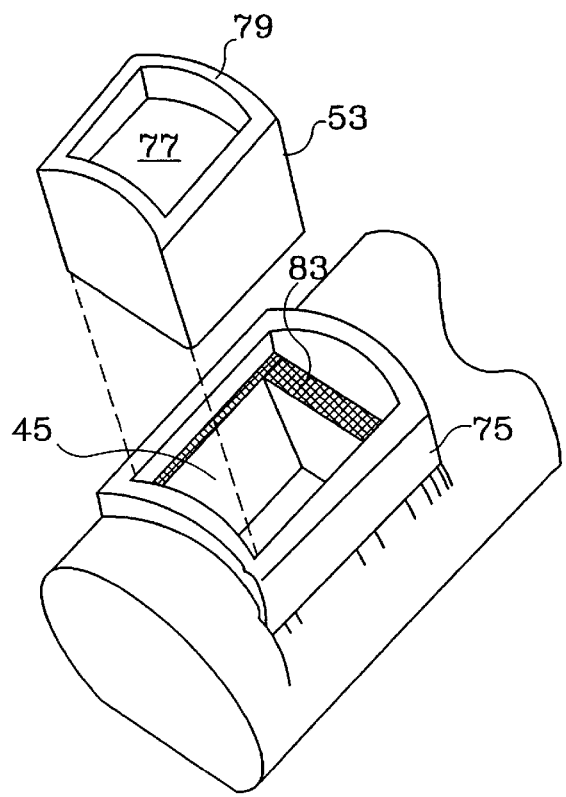

Referencing FIGS. 5, 6 and 7, it can be seen that the ISFET housing back hole 45 has a integral circumferential collar 75 extending outwardly from the outer edge of a shoulder 83 extending between the back hole 45 and the collar 75. The back hole 45 and its area leading to the central bore 55 are shaped to accept and secure in a press fit manner the back plug 53 (FIG. 6). The back plug 53 is radiused at its outside surface 77 to be substantially similar to the radius of the outside wall of ISFET housing 33 which is of a substantially cylindrical shape. Extending from the outside surface 77 of the back plug 53 is a integral circumferential collar 79. The back plug 53 is composed, in a preferred embodiment of the pH sensor 31 of a graphite filled, engineering grade thermoplastic plastic, to be electrically conductive. By using a conductive back plug placed in electrical contact with printed wiring runs 41 of the PCB 37, an electrical field can be generated at the plug 53 thereby eliminating the need for a separate electrical wire exiting the body and possibly causing further sealing problems.

Once the back plug 53 is press fit into ISFET housing back hole 45, the circumferential collar extensions of each member are aligned with a space therebetween comprising a well 85 between the collar extensions 75,79 whose bottom is the shoulder 83. A heat stake anvil 87 of the proper radius to serve as a molding element for the desired final shape, in this case flush and cylindrical, is then brought down to melt the housing and plug collar members together. The collar material then melts and flows into the well 85 whereupon the anvil 87 is brought to below melt temperature to set the plastic, and then removed, thereby providing a substantially flush outer wall with a hermetic seal in the back hole area of the ISFET housing 33. In the preferred embodiment the plug collar 79 is designed to melt away from the plug 53 and blend with the body material to ensure that conductive thermoplastic material remains at the surface 77. Relief areas 89 are further provided in the housing body (FIG. 6) as a catch basin for collar melt material to maintain a flush housing body outer wall. Other shapes, such as the rectangular block of FIG. 9, may lack the radius of the preferred embodiment and be less conducive to a noncovering application of the plug 53 and/or lack relief areas for provision of a flush exterior finish, but will still provide the hermetic seal necessary for proper functionality while eliminating the need for potting with epoxy.

Figure 1B:
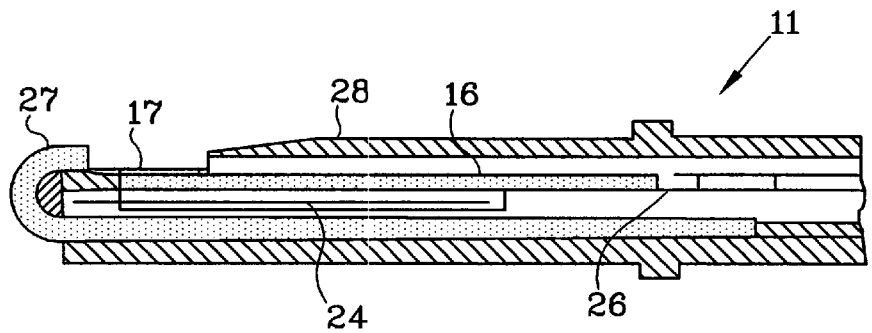

At this point, all components of the pH sensor 31 are substantially locked in place and any necessary environmental sealants such as heat shrink, plastic or the like are placed over the PCB in preparation for the final sealing of the probe casing 43 (FIG. 1) which is snap fit over locking channels 81 of the ISFET housing 33.

Figure 8:
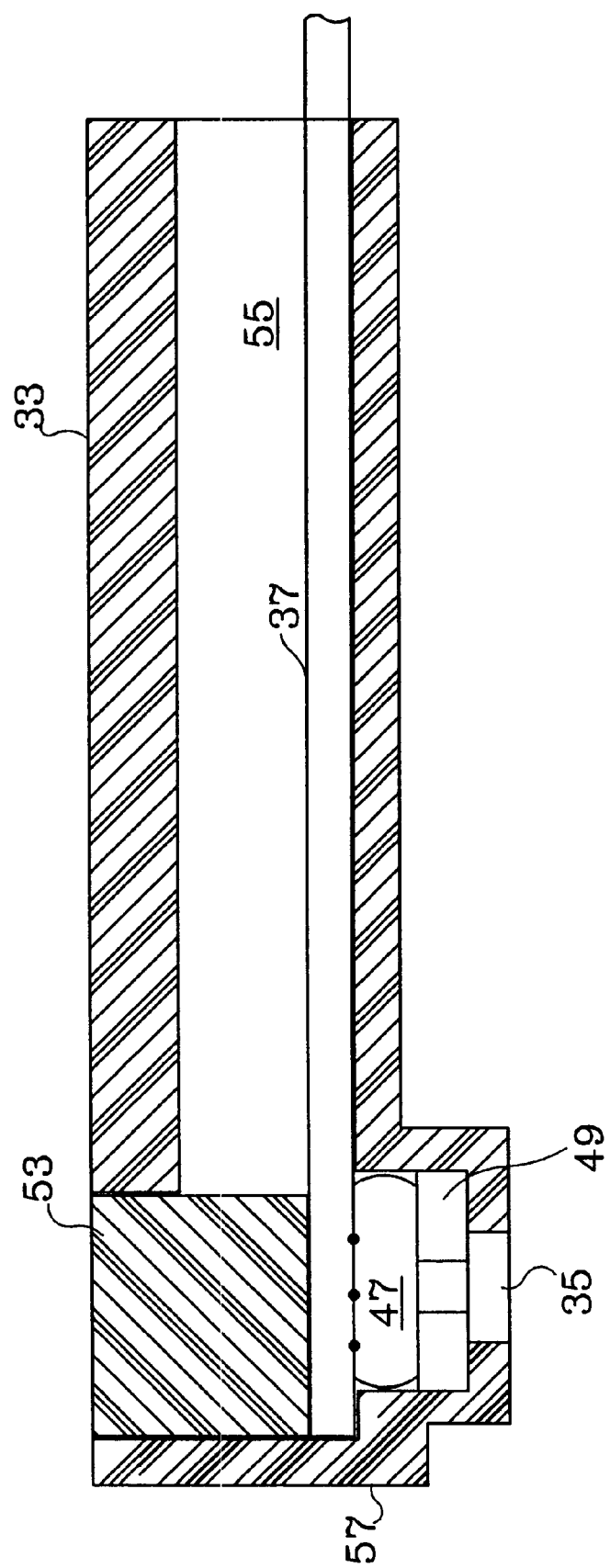
FIG. 8 illustrates an alternative embodiment wherein the ISFET is bonded directly to the PCB eliminating the need for the second conductive seal.

An alternative embodiment, FIG. 8, shows that the ISFET 47 may be attached directly to the PCB 37 by solder bumping or the like. The back plug 53 then forces the PCB 37 into the media seal 49. The media seal 49 is placed in alignment with the media through-hole 35 and the PCB enters the central bore 55 of the housing 33 in the above-described manner.

Figure 9:
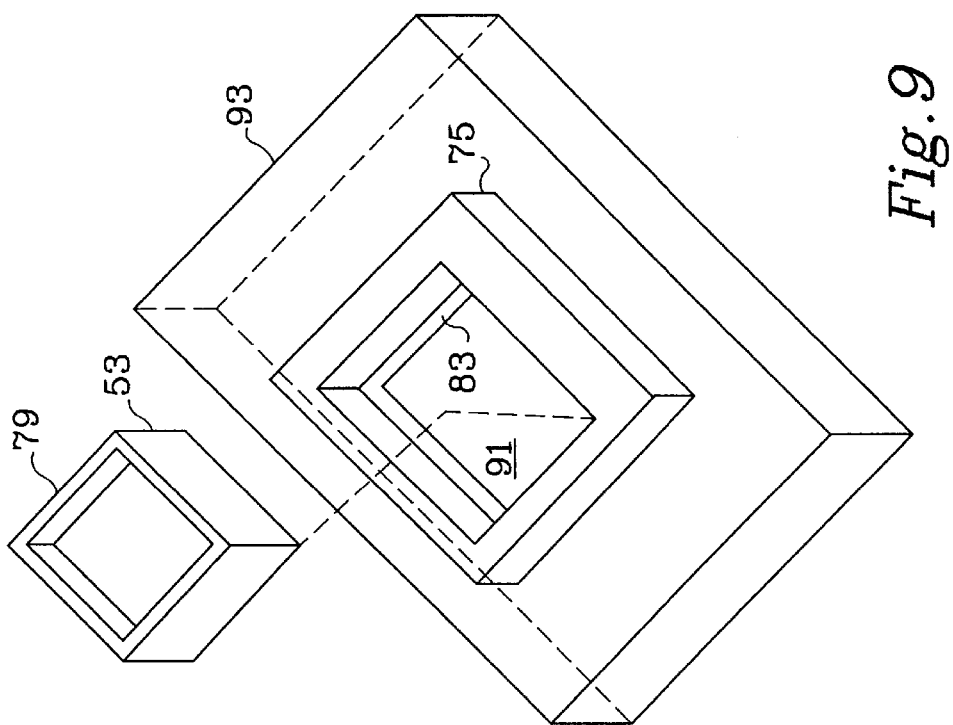
FIG. 9 is a schematic representation of a sensor packaging apparatus without regard for a port to the external environment.
Figure 10:
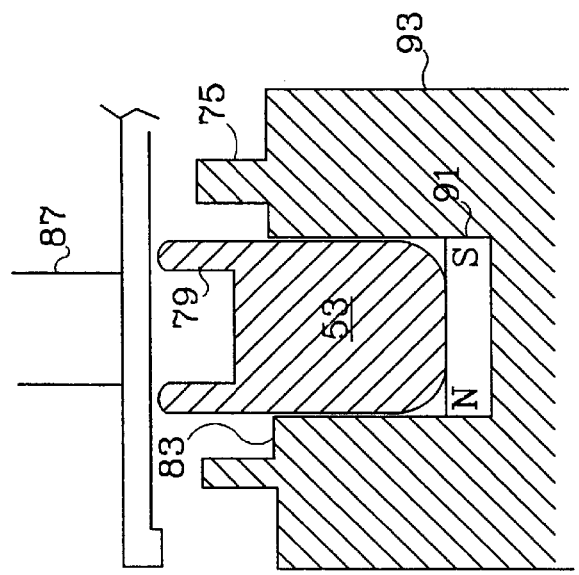
FIG. 10 is a cross section of FIG. 9.

As seen in FIGS. 9 and 10, the heat staking technique of the present invention in equally applicable to encapsulating items where no sensing port to the external environment is needed. For example, in a magnetic sensor element where a magnet needs to be efficiently encapsulated with high accuracy in a thermoplastic body 93, the use of the mechanically locked plug 53 having an integral circumferential collar 79 spaced at appropriate distance from the mating circumferential collar of the body 93 will allow hermetic encapsulation by heat staking according to the present invention.

Although the present invention has been described to illustrate a specific embodiment, it should be understood that alternative embodiments are also within its scope.

The embodiments of the invention in which an exclusive property or right is claimed are defined as follows:

1. A sensor package comprising:
   a. a thermoplastic housing having a void for receiving a sensor component therein and a back hole in fluid communication with the void constructed and arranged to admit the component therethrough;
   b. a thermoplastic plug mechanically fixed within the back hole for loading the sensing component in place within the void;
   c. the housing and plug being constructed and arranged to hermetically seal together upon the application of heat thereto.

2. The sensor package according to claim 1 further comprising:
   an integral circumferential collar extending from a surface of the plug for receiving the application of heat.

3. The sensor package according to claim 1 further comprising:
   an integral circumferential collar extending from a surface of the housing for receiving the application of heat.

4. The sensor package according to claim 1 further comprising:
   resilient means for cushioning the sensing component from the loading force of the plug.

5. The sensor package according to claim 1 wherein, the package further comprises:
   integral means for creating a hermetic seal substantially flush with the exterior of the housing.

6. The sensor package according to claim 5 further comprising:
   an integral circumferential collar extending from a surface of the plug for receiving the application of heat.

7. The sensor package according to claim 5 further comprising:
   an integral circumferential collar extending from a surface of the housing for receiving the application of heat.

8. The sensor according to claim 5, further comprising:
   a. a first integral circumferential collar extending from an outside surface of the plug;
   b. a second integral circumferential collar extending from an outside surface of the housing outer wall surrounding the back hole and;
   c. said first and second integral collars being fused together during the application of heat thereto.

9. The sensor package according to claim 8 wherein:
   the housing has a recessed area adjacent the second integral circumferential collar for receiving melted collar material upon the application of heat.

10. The sensor package according to claim 8 wherein:
    the first and second integral circumferential collars create a well therebetween when the plug is mechanically fixed within the backhole, the well providing a space for receiving melted collar material upon the application of heat.

11. An ion sensitive probe comprising:
    a. a housing having a central bore and a first end open to the central bore, and a media hole and a back hole in the housing in fluid communication with the central bore, and a well communicating with the media hole;
    b. a elastomeric media seal, having a through-hole therein in fluid communication with the media hole, said elastomeric medial seal fitted within the well for hermetically sealing the fluid passage through the media hole to the central bore except by way of the through-hole;
    c. an ion sensitive semiconductor within the well having a first side with a sensing area and a second opposing side with patterned electrical leads in electrical communication with the sensing area, the sensing area in fluid communication within the media seal through-hole;
    d. a PCB, with electrical leads on a first surface thereof, extending through the first housing opening and the central bore, at least some of the PCB electrical leads on the first surface of the PCB contacting the ion sensitive semiconductor;
    e. a thermoplastic plug constructed and arranged to be mechanically locked in the back hole so as to press the media seal in to a hermetically sealed position within the housing; and
    f. the plug being constructed and arranged to hermetically seal the backhole upon the application of heat thereto.

12. The ion sensitive probe according to claim 11 further comprising:
    an integral circumferential collar extending from the surface of the plug for receiving the application of heat.

13. The ion sensitive probe according to claim 11 further comprising:
    an integral circumferential collar extending from the surface of the housing outer wall for receiving the application of heat;
    the housing wall being composed of thermoplastic material.

14. The ion sensitive probe according to claim 11 further comprising:
   a. a first integral circumferential collar extending from a surface of the plug intended to mate with a housing outer wall;
   b. a second integral circumferential collar extending from a surface of the housing outer wall surrounding the back hole; and
   c. said first and second integral collars being fused together during the hermetic sealing process.

15. The sensor package according to claim 14 wherein:
   the housing has a recessed area adjacent the second integral circumferential collar for receiving melted collar material upon the application of heat.

16. The sensor package according to claim 14 wherein:
   the first and second integral circumferential collars create a well therebetween when the plug is mechanically fixed within the backhole, the well providing a space for receiving melted collar material upon the application of heat.

17. The ion sensitive probe according to claim 14 wherein the collars have a space therebetween before the hermetic sealing process.

18. The ion sensitive probe according to claim 11, further comprising:
   an elastomeric conductive seal within the well having patterned conductors extending from a first side thereon to a second side, the conductive seal conductors of the first side being in electrical communication with the patterned electrical leads of the ion sensitive semiconductor.

19. The ion sensitive probe according to claim 11, further comprising:
   a means for sealing the central bore first end.

* * * * *